United States Patent [19]

Berque

[11] Patent Number: 6,020,333

[45] Date of Patent: *Feb. 1, 2000

[54] COMPOSITIONS CONTAINING IN PARTICULAR, RIBOFLAVIN, FOR THE LOCAL PREVENTION OF DISEASES OF THE GENITAL AND RECTAL MUCUS MEMBRANES

[76] Inventor: Jean Berque, 57 rue Henri-Fichon, F-16100 Cognac, France

[*] Notice: This patent issued on a continued prosecution application filed under 37 CFR 1.53(d), and is subject to the twenty year patent term provisions of 35 U.S.C. 154(a)(2).

[21] Appl. No.: 08/564,316

[22] PCT Filed: Apr. 11, 1995

[86] PCT No.: PCT/FR95/00463

§ 371 Date: Dec. 18, 1995

§ 102(e) Date: Dec. 18, 1995

[87] PCT Pub. No.: WO95/27491

PCT Pub. Date: Oct. 19, 1995

[30] Foreign Application Priority Data

Apr. 11, 1994 [FR] France ................... 94 04232

[51] Int. Cl.[7] .......................... A01N 43/60; A01N 43/08; A01N 43/16; A01N 27/00
[52] U.S. Cl. .......................... 514/251; 514/457; 514/474; 514/458; 514/358; 514/763
[58] Field of Search .................... 514/457, 251, 514/474, 458, 358, 763

[56] References Cited

U.S. PATENT DOCUMENTS 5,366,440 11/1994 Fossel ........................... 604/4

OTHER PUBLICATIONS

Isaacs et al 112 CA:112053g 1990.
Harukeh et al 113 CA:184287e 1990.
Child et al 108 CA 109452y 1988.
Totani et al 116 CA 99299c 1992.
Merchk Index 10th Ed 1985 # 5457 & 8338.
Jamison et al 110 CA: 209216j 1989.
Roedenen et al PNAS vol. 87 pp. 4884–4888 1990.

Primary Examiner—Russell Travers
Attorney, Agent, or Firm—Bierman, Muserlian and Lucas

[57] ABSTRACT

The invention relates to the field of therapeutic chemistry and concerns novel antiviral pharmaceutical compositions for the local prevention of diseases of the genital and rectal mucus membranes. The compositions are characterized in that that the active ingredient used is riboflavin or one of the mineral or organic acid or FAD addition salts thereof. The active ingredient further comprises niacin or NAD or NADP. Vitamin factors can also be added such as carotene, flavonoids, acetyloenzyme A and vitamins A, E, C, B6, B8 or F. Fillers such as insoluble barium salts, titanium derivatives, alkaline-earth silicates, aluminium silicates, mineral or organic bismuth salts, insoluble zinc salts, rare earth derivatives, zirconium derivatives, can be added to said compositions to reinforce the mucus adhesiveness of said preparations. Vegetable extracts containing flavonoids or anthocyanosides can be further incorporated into the pharmaceutical compositions of the invention. The preferred pharmaceutical preparations take the form of creams, gels, lotions, viscous emulsions, suppositories, ovules, capsules, vaginal tablets and the like. The initial claimed effect is primarily the prevention of sexually transmissable viral diseases, namely AIDS, genital herpes and the papillomavirus.

7 Claims, No Drawings

COMPOSITIONS CONTAINING IN PARTICULAR, RIBOFLAVIN, FOR THE LOCAL PREVENTION OF DISEASES OF THE GENITAL AND RECTAL MUCUS MEMBRANES

This application is a 371 of PCT/FR95/00463 filed on Apr. 11, 1995. In its patent application Ser. No. 92.12180, filed on Oct. 2, 1992, the applicant has already described the use of riboflavin in the manufacture of condoms and gloves for the medico-surgical protection.

The use of condoms intended for the prevention of sexually-transmissible diseases and namely the diseases due to HSV2 and HIV viruses, as well as the genito-anal infections due to papillomavirus does not appear to obey to the prophylactic sanitary recommendations. This restriction in the use in connection with socio-economic, technical or sexual reasons, lead to propose some other solutions to limit the venereal propagation and count. The use of salves, vaginal suppositories and suppositories made of biological and not toxic anti-viral molecules seems to supply with a response ot this need. Such an alternative appears to be more especially as advantageous, the used molecules may further show anti-inflammatory, anti-allergic, anti-bacterial, anti-fungal, immonostimulating and healing properties. Some tests with chemical synthetic molecules with anti-viral activity have been performed. So have been proposed sponges based on nonoxynol-9 with the aim to be both contraceptive and virulicide. These tests are far to be conclusive from a point of view of efficacy and moreover the products to be used produced micro-lesions of the vaginal wall. Once again experimentation carries the proof of the existing gap between "in vitro" efficacy then "in vivo" efficacy and tolerance. This invention has thus as a subject matter a composition based on biological molecules having shown an "in vitro" anti-viral activity but being totally non toxic and even displaying local curative properties due to recovery of the cell respiratory chain, the equilibrium of oxydo reduction and the healing of the mucosal microlesions from carential origin.

Consequently, this invention has as a subject matter novel pharmaceutical compositions having anti-viral action intended for the local protection of the genital and rectal mucosae, wherein they contain as an active ingredient, riboflavin and/or one of an acid addition salt thereof with a mineral or organic acid and/or FAD.

The active ingredient may be further added with Niacine and/or NAD and/or NADP. They may be also added vitaminic factors, such as carotenoids, flavonoids, acetylcoenzyme A, vitamins A, E, C, B6, B8 and/or F.

It may be also added to the compositions filling agents which increase adhesiveness of the preparations to the mucosae such as insoluble salts of baryum, titanium derivatives, earth alkaline silicates, mineral or organic salts of bismuth, insoluble salts of zinc, derivatives of rare earths, derivatives of zirconium.

It may also be possible to incorporate to the pharmaceutical compositions according to this invention, vegetal extracts containing flavonoids or anthrocyanosides.

The preferred pharmaceutical compositions are the creams, the gels, the milks, the viscous emulsions, the suppositories, the vaginal suppositories, the capsules, the vaginal tablets and the like.

The initial effect relates at first in preventing the viral sexually transmissible diseases (AIDS, genital herpes, papillomavirus). However, if the same mixture both may be curative and offer complementary properties, it is a matter of undeniable advantage. It will substantially be antibacterial, antifungal, antiparasitic, anti-allergic and anti-inflammatory actions, trophic effects, healing effects and finally vasculotropic effects.

Riboflavin and FAD (or FADH2) may be used alone. However, complementary and action synergy brought by Niacin and its active forms, acetylcoenzyme A, Vitamins A, E, C, biotin, flavonoids, carotenes are interesting to take into consideration. The addition of pyridoxal-5-phosphate and of N5-methyl tetrahydrofolate may be useful.

Such a composition having anti-oxydising polarity is intended to be applied or introduced at the level of mucosae, depending on the knowledge of the pharmacokinetics and of the galenical pharmacy.

The preparations intended to the local application will be offer in the form of ointments, gels, creams, foams or any other preparations issued from the recent galenical pharmacy. The preparations intended for endo-vaginal or endo-rectal insertion are of about the same constitution than the foregoing ones but may also be vehiculed by vaginal suppositories, suppositories, sponges, soft gelatine capsules, tablets and any other container having a micro-diffusion.

Whatever is the form to be used, the essential goal will be to show an optimal efficacy/tolerancy relationship. This form has thus to combine protecting, anti-oxydizing and antiviral effects, and also complementary trophic effects, healing and immunostimulating effects even antifungal and antibacterial actions which will constitute un-neglegible advantages.

The covering effect is interesting to consider according a double aspect it is at first able to constitute a barrier against the diffusion of the virus and the proteins they synthetize. It may further play a role of an electromagnetic filter-screen which will both block the UVC, the X-rays and the IR.

According to the applicant, the double helix of the DNA of the cells and of the retroviruses would be the concrete form of the double tore generated by the synchrone oscillating motions of the electric field and the magnetic field which join the light and are perpendicular each to the other. Such a structure with the ADN double strand included in a nucleus the membrane of which is caracterized with the presence of pores, is analogous to a amplifying triod absorbing ultra violet radiations and re-emetting infra red radiations.

The fact of blocking the UV-C the wawe lenghts of which corresponding to the viral dimensions and the IR re-emitted would inhibit the activation indeed the viral synthesis (UV-C) then the transmission of viral information remotedly (IR).

It further appears of interest to foresee the incorporation in the intended preparation, of opaque matters such as baryum or titane derivatives. The filters with baryum allow the UV-A and UV-B to pass but absorb the UV-C and X rays. For this reason, baryum sulphate formed of particles of 1 micron size show a big covering potency and lines the smallest recesses of the mucosa.

According to the applicant, baryum derivatives represent an addition to the choice of riboflavin. The baryum derivatives emit in the flamme a yellow-green colour. This colour is complementary to the wawe lenghts corresponding to red and those immediately higher which correspond to the infra-red. Baryum which is not very toxic, arrests UV-C and the IR rays. It seems to represent an element of value in the local protection of the mucosae against viruses. As an example, baryum titanate is one of the most performing isolating agents. The combination of titanium derivatives or baryum derivatives to riboflavin, seems to be very advantageous for several reasons. It protects at first the membrans against the farthest radiation which are pathogenic and, more particularly, against the energy-rich ultra violets (UV-B and UV-C) and the most frequential infra-red radiations (1,5 to 0,8 micron). The applicant has already expressed the assumption according to which the viruses may, due to their dimensions, be in phase with the UV and namely with the UV-C, thus achieving a perfect resonance. An excessive oxydation in relation with UV-C would activate the viruses. Alternatively, processes of excessive fermentation bound to an excessive infra-red rebound would stimulate the bacterial and fungal growth. Therefore, the combination titanium-baryum-riboflavin constitutes a screen for the farthest UV and IR radiations and thus acts both as a viral, bacterial, fungal and parasitic inhibitor. Such a combination is at the same time anti-allergic.

The above mixture is moreover anti-inflammatory due to its anti-oxydizing properties bound to those already described. The further interest of the complex titanium-baryum-riboflavin relates the mitochondrial membrans of the cells because their lamellar bi-layer structure. Titanium and baryum will dope the membranar semi-conductor and strongly catalysed the charges transfert between cytochromes which carry the electrons and oxygen, and the protons pump. At the level of the immunitary system, it thus constitutes an amplifyier of the synthesis of antibiotics. It may therefore be considered as an immunostimulant.

The titanium derivative may be incorporated to the anti-oxydizing and photoprotective complex and be used at least in three different forms: titanium dioxyde, titanium chloride and titanium mica. The chloride form has the further interest to restrain the infra-reds. Extrapolation of these properties at the level of anti-viral photosensitive molecules and more particularly to the level of riboflavin, seems to be of the highest interest. Chlorine and the halogens saturate, at the level of unsaturated fatty acids, the ethylenic double bonds and thus modulate the lipids β-oxydation.

According to the applicant, the p-oxydation alternatively activated by $Ca^{++}$ and by $hg^{++}$, participates to the opening and to the generation of membranar channels. Chlorine, while saturating some phospholipidic chains, thereby would modulate the number and the frequency of the channel openings. Whilst the UVs show a determined tropism for the ethylenic double bonds, the saturated fats constitute a screen for the same radiation UV. Now, most of the elements and molecules defined along this invention, have been selected for their anti-oxydizing action. They play, nearly all of them, in fact a role of oxydo-reducers. Indeed if oxydation is toxic for the cells due to the generationof free radicals, it is generally needed. It is at first useful for the production of a gradient of electric charges and for the circulation of electrons and protons. It is also compulsory to the catabolism of the foods, to the cells respiration and to the phosphorylation which are oxydative processes. It will further play a paramount role in the stimulation of some mechanisms of defence of the body. It is thus why the peroxides and more precisely the singulet oxygen, characterized by its chemoluminescence, its very short span of life, and its high agressivity—will destroy the pathological cells which have passed a threshold of lethality. Oxydation would stimulate on the other part at the level of leukocytes and namely macrophages, an enzyme the role of which seems to be especially dedicated to the destroying of micro organisms which are agressive.

NADP-oxidase is a B2 and PP depending flavo-enzyme.

The destroying of pathogenic agents such as bacterias and viruses, may in some other cases, obey to biochemical processes and mainly to the production at the level of leukocytes, of hypochlorous ions $OCl^-$. The anti-oxydizing agents have the caracteristics to transform peroxides into hydroperoxides the span of life of which is much longer and clearly less pathogenic.

The mica-titanium is used in the sun creams for its photo reflecting properties. Mica is an aluminium silicate. Similarly to titanium and baryum, aluminium and silicium are closely complementary. They constitute in parallel a semi-conductive, semi-screening, and piezo-electric system which alternatively acts as a screen and an isolator then as an optoelectronic conductor.

At the level of the membran semi-conductors and transistors the couple silicium-aluminium plays a equivalent role than the couple baryum-titanium. It stops the farthest opto-electronic pulses which are pathogenic and catalyses "a contrario" the transfert of appropriate energies. It constitute therefore an anti-oxydizing agent and simultaneously a doping of the respiratory exchanges. This mechanism of action partially explains the trophic and healing properties of silicium and aluminium on the skin and mucosae. Aluminium is at first very sensitive to oxydation but it will be very shortly coated with a film of aluminium hydroxide which is very resistant. Such properties are fondamental at the level of the claimed anti-oxidizing composition, particularly for its anti-viral and anti-methhemoglobinizing properties. Other metals and metalloids have a determined interest in virtue of their anti-oxidizing catalytic properties (enzymatic activators and/or membranar doping agents) as well as their role of opto-electronic filter-screen and of frequential modulator.

According to the applicant, a high level of LDL cholesterol is the standard of an auto-immune threat. Some authors have expressed the hypothesis according to which the viruses and particularly the viruses of herpes would induce an atheromatosis "Viral Theory of Atheromatosis—Place of cytomegalovirus" J. Byad and coll. Ann. Biol. Clin. (1993) 51.101–107. According to the applicant's assumptions, the viral infection and atheromatosis would not be directly interdependant. They would in fact be two adjoined pathologies which would attest to the fact that the organism suffers from an oxydative stress.

The theory of two closely related pathologies seems to be corroborated by the fact the anti-viral therapy studied by the applicant and consisting of photoprotective and anti-oxidizing biological molecules simultaneously shows anti-atheromatous properties. It thus allows to counteract the oxydative stress and the responsible auto-immune disease.

As far as the protection of genito-anal mucosae is concerned, the aimed effect being at short term, it is preferable to use saturated fats which confer to the composition a covering photoprotective and anti-oxidizing potency. These saturated fats may be used as a carrier for the liposoluble vitamins i.e. substantially for the carotenes, such as p-carotenes, canthaxanthin, vitamin A as the aldehyde or the acid, and a-tocopherol acetate (vitamin E). The saturated fats may well consist in straight-chain fatty acids with more than 8 carbon atoms, such as for example palmitic acid ($C_{16}$), arachidic acid ($C_{20}$) and cerotic acid ($C_{26}$) as well as branched-chain fatty acids among which lanolin esters and lanolin itself. It includes also the cholesterol precursors such as squalenes which may also be saturated by hydrogenation or halogenation, lanosterol which is riched in methyl groups and finally cholesterol itself.

In the whole, the active ingredient which may be incorporated into the claimed composition includes: vitamin B2, PP, B6, B8, B9, A, E, C, the carotenes (β-carotene, canthaxanthin), acetylcoenzyme A, and the flavonoids. In the event that the local metabolic conditions would not allow to transform the basic formulations into active formulations, it would be wishable to deliver these directly in the oxydated form or preferably in the reduced form. FAD and, at the most, FADH2 could complement riboflavin. NAD, NADH2, NADP and NADPH2 would complement Niacin; pyridoxal-5 phosphate and N5-methyl tetrahydrofolate would for the same reason preferable to pyridoxin and to folic acid.

Amino acids such as cystein or N-acetylcystein, and peptides such as glutathion and lysozyme show an interest as a complement.

Saturated fatty acis with straight chain (palmitic acid, arachidic acid, cerotic acid) or branched chain (lanolin, esters of lanolin) or cyclic chain (squalenes, lanosterol, cholesterol) are interesting for their photoprotective properties and their role of carrier for liposoluble vitamins.

The metals which appear as the most complementar ones to the already cited active ingredients are the baryum salts (sulphate, titanate), titanium derivatives (chloride, dioxide, and mica-titanium), silicium derivatives and aluminium derivatives (aluminium silicate, aluminium hydroxide), chloride, fluorine, sulphur, manganese, zinc, zinc oxide, catalytic ionized zinc) as well as moreover metallic derivatives, silver, almost in the form of colloidal silver and also calcium and magnesium.

Plants such as melilot, bilberry and Saint John's wort may well appear as not being essential. However, Saint John's wort may represent an additive of choice in the form of fresh flowery ends of Hypericum perforatum as an oily macerate as well as its active principle, hypericine with the assumption that this compound will not be to much allergenic.

Adding Lysozyme and saturated fats is not perhaps essential but they are totally capable to potentialize the required effects.

Among the metals, the addition of which is foreseen, the following ones are preferred: baryum, titanium, silver, selenium, germanium, zinc, chlorine and fluorine.

The utilized dosologies for these various compounds will be about: 10 to 200 mg for riboflavin, 300 to 500 mg for niacin (they will be less for the active ingredient) 500 mg to 1 g for pyridoxine, 500 mg to 1 g for vitamin C 20 to 100 mg for folic acid, 20 to 100 mg for acetylcoenzyme A, 50 to 100 mg for biotin, 20 to 50 mg for β-carotene and for canthaxantine, 25 to 100.000 UI for the vitamin A, 20 to 100 mg for vitamin E (tocopherol acetate), 20 to 50 mg for lysozyme, 100 to 300 mg for melilot, bilberry and for Saint John's wort (the doses are less for the active ingredients such as hypericin).

From few μg to some mg for the metals utilized in a goal for activation (chlorine, selenium, aluminium), these are used at a dosis of hundreds of mg, even in the amount of several gramms when they are used for their covering properties (zinc oxide, aluminium hydroxide, baryum sulphate).

The various galenical forms the listing and the description of which will follow, may be utilized as an adjuvant of the condoms and outside of their uses, with both a preventive and curative aim. They shall present a maximal covering power but which does not impede the diffusion, bioavailability, and efficacy of the active ingredients. These latter ones will be more especially interesting as they will have a more longer life span. The use and the follow up of the galenical compositions incidentally need some formulations which are practical and which are devoid of unpleasant draw backs (odour, discharges).

The covering power will have as an aim, not only to line the cutaneo-mucous coating to constitute a material barrier, but also to constitute a a screen against the electrical radiations.

As it has been previously shown, these radiations will be both viral (UV-C) and bacterial, fungal etc . . . (IR) activators. They would further transmit a remote emission i.e. the frequential information from hycoproteic origin sent out by the viruses (IR) such a material and electromagnetic screen, will be still more interesting when it behalves as a semiconductor and thus catalyses the respiratory and metabolic exchanges. Baryum sulphate—optionnally enriched with titanium—seems to be wholly appropriate to this definition. The same thing applies for aluminium silicate. Other compounds play an important role such as aluminium pectate, zinc oxide, retinol palmitate, lanoline for their covering power. The active ingredients of the claimed compositions may be carried by a fatty phase for the liposoluble vitamins (carotenes, vitamin A and vitamin E) and by an aqueous or hydroalcoholic phase for the water soluble vitamins (B2, PP, B6, C), for lysozyme, glutathion, plants such as Saint John's wort, as well as some metals such as silver, zinc, manganese, etc . . . .

The whole content may be incorporated into active liposomes coated with a thin film to be resorbed, made of aluminium silicate, in the case of vaginal mucosal wounds. The fatty layer, underlaying to the film of silica and coloured in orange-yellow by the carotenes, vitamin A and vitamin E, would be in the same way polarized to the diseased zones of inverse electromagnetic polarity. Within the liposomes, the water soluble vitamins and particularly riboflavin would be protected from oxydation with vitamin C, zinc, manganese, etc . . . . The central core of the liposomes might—for its part—be constituted of baryum silicate and titanium silicate which would thus constitute in the last instance the covering barrier.

The active liposomes, previously described, might constitute the structural basic unit of a gel for penial, vulvovaginal or rectal use (with an uni-dosis tube with canule). They also might to be included into vaginal suppositories, soft gelatine capsules, or slow-release tablets as well as in suppositories.

The enumeration of the galenical forms is provided by way of illustration without limiting the invention.

What is claimed is:

1. A method of treating or preventing sexually transmitted viral infections in humans comprising topically applying to the mucosa of the penis the vulva, the vagina, or the rectum of humans an antivirally effective amount of a dermatological composition consisting essentially of an antivirally effective amount of Riboflavin or a non-toxic, pharmaceutically acceptable acid addition salt thereof alone or in combination with FAD to prevent transmission of a sexual disease without any systemic action.

2. The method of claim 1 wherein the composition additionally contains at least one member of the group consisting of niacin, NAD and NADP.

3. The method of claim 1 wherein the composition additionally contains at least one member of the group consisting of carotenes, flavonoides, acetyl co-enzyme A and vitamins A, E, C, B6 AND B9.

4. The method of claim 1 wherein the composition additionally contains lysozyme.

5. The method of claim 1 wherein the composition also contains glutathion and N-acetylcystein.

6. The method of claim 1 wherein the composition also contains a long chain saturated fatty acid.

7. The method of claim 1 wherein the composition also contains a member selected from the group consisting of barium, titanium, silica, aluminum, manganese, zinc, selenium, germanium, nickel, silver, calcium, magnesium, sulfur, chlorine and fluorine and salts thereof.

* * * * *